United States Patent
Wood-Putnam et al.

(10) Patent No.: US 8,336,536 B1
(45) Date of Patent: Dec. 25, 2012

(54) ACTIVE HEATING SYSTEM FOR UNDERWATER DIVER

(75) Inventors: Jody Wood-Putnam, Panama City Beach, FL (US); Marshall Lew Nuckols, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1088 days.

(21) Appl. No.: 12/214,725

(22) Filed: Jun. 23, 2008

(51) Int. Cl.
*A61F 7/00* (2006.01)

(52) U.S. Cl. ........................................ 126/204; 607/114

(58) Field of Classification Search ................ 607/114, 607/96, 104, 110, 111, 109, 113; 165/46, 165/47, 48.1; 2/2.15, 2.16, 69, 69.5, 70, 2/82, 87, 135; 126/204, 36; 220/577; 36/2.6; 128/201.27; 73/865.1
See application file for complete search history.

(56) References Cited

U.S. PATENT DOCUMENTS

| | | | | |
|---|---|---|---|---|
| 3,229,681 A | * | 1/1966 | Gluckstein | 126/204 |
| 3,367,319 A | * | 2/1968 | Carter, Jr. | 126/204 |
| 3,385,286 A | * | 5/1968 | Jones | 126/204 |
| 3,644,706 A | * | 2/1972 | Larenzo et al. | 219/211 |
| 3,688,762 A | * | 9/1972 | Chi et al. | 126/204 |
| 3,730,178 A | * | 5/1973 | Moreland | 128/201.21 |
| 3,875,924 A | * | 4/1975 | Bayles | 126/204 |
| 3,884,216 A | * | 5/1975 | McCartney | 126/204 |
| 4,119,082 A | * | 10/1978 | Miyamori et al. | 126/263.05 |
| 4,205,957 A | * | 6/1980 | Fujiwara | 44/250 |
| 4,223,661 A | * | 9/1980 | Sergev et al. | 126/204 |
| 4,264,362 A | * | 4/1981 | Sergev et al. | 75/243 |
| 4,430,988 A | * | 2/1984 | Krasberg | 126/206 |
| 4,503,850 A | * | 3/1985 | Pasternak | 128/201.25 |
| 4,522,190 A | * | 6/1985 | Kuhn et al. | 126/263.02 |
| 5,029,572 A | * | 7/1991 | LeBlanc | 126/204 |
| 5,084,986 A | * | 2/1992 | Usui | 36/2.6 |
| 5,674,270 A | * | 10/1997 | Viltro et al. | 607/112 |
| 6,264,681 B1 | * | 7/2001 | Usui | 607/111 |
| 6,347,627 B1 | * | 2/2002 | Frankie et al. | 128/201.21 |
| 7,306,403 B1 | * | 12/2007 | Sanders | 405/186 |
| 7,383,592 B2 | * | 6/2008 | Nuckols et al. | 2/161.1 |
| 2002/0056451 A1 | * | 5/2002 | Frankie et al. | 128/201.21 |
| 2002/0164473 A1 | * | 11/2002 | Buckley | 428/308.4 |
| 2006/0217790 A1 | * | 9/2006 | Ota et al. | 607/114 |
| 2007/0106353 A1 | * | 5/2007 | Carstens | 607/112 |

* cited by examiner

*Primary Examiner* — Kevin C Sirmons
*Assistant Examiner* — Michael J Anderson
(74) *Attorney, Agent, or Firm* — James T. Shepherd

(57) ABSTRACT

An active heating system for an underwater diver uses material particles that can generate heat in an exothermic reaction in the presence of oxygen. The material particles are positioned at selected region(s) within an underwater diver's attire. A source of oxygen gas is coupled to the selected region(s).

17 Claims, 3 Drawing Sheets

ACTIVE HEATING SYSTEM FOR UNDERWATER DIVER

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to heating systems for underwater divers, and more particularly to an active heating system that can be used to heat one or more regions within a diver's wetsuit or drysuit.

BACKGROUND OF THE INVENTION

In cold environments, a person's hands and feet will typically get cold first. Accordingly, a variety of lined gloves and boots are available for people performing activities in cold-air environments. In addition, commercially-available chemical hand and foot warmers can be inserted into one's gloves and/or boots. These hand and foot warmers are small gas-permeable pouches that contain particles of materials that generate an exothermic reaction in the presence of oxygen. The active ingredient in many of these products is iron "particles" (e.g., shavings, filings and/or powder) that provide a heating source through a process of accelerated rust. That is, the iron particles oxidize in the presence of oxygen to produce iron oxide. This reaction is exothermic and lasts for several hours as long as there is a steady supply of oxygen as is the case in the ambient air environment. Most gloves and boots allow for sufficient air infiltration to maintain this exothermic reaction.

In underwater environments, divers wear wetsuits or drysuits that cling to one's skin thereby minimizing any air space between the diver and the suit. Furthermore, the underwater environment does not have a ready supply of oxygen. Accordingly, the above-described commercially-available hand and foot warmers are of no value to an underwater diver.

SUMMARY OF THE INVENTION

Accordingly, it is an object of the present invention to provide a heating system for an underwater diver.

Another object of the present invention is to provide a heating system that can be incorporated into a diver's gloves and/or boots.

Other objects and advantages of the present invention will become more obvious hereinafter in the specification and drawings.

In accordance with the present invention, an active heating system for an underwater diver uses material particles that can generate heat in an exothermic reaction in the presence of oxygen. In general, the material particles are maintained at a selected region within an underwater diver's attire. A source of oxygen gas is coupled to the selected region so that the oxygen gas can be introduced to the selected region. Typically, the selected regions are defined in a diver's gloves and/or boots.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
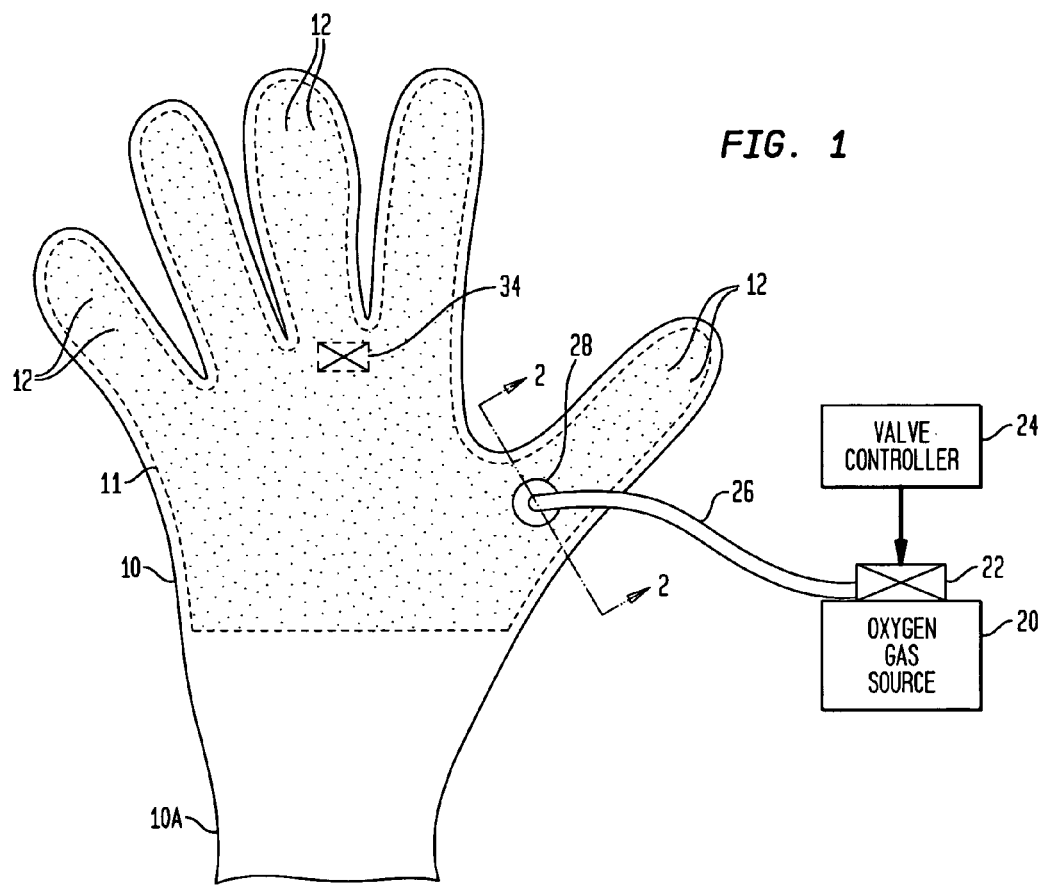
FIG. 1 is a schematic view of an active heating system for an underwater diver's glove in accordance with an embodiment of the present invention.

Referring now to the drawings and more particularly to FIG. 1, an active heating system for an underwater diver's glove 10 is shown. Diver's glove 10 is any conventional glove suitable for use in underwater diving applications. Typically, glove 10 is part of a diver's wetsuit or drysuit attire that is donned after a diver puts on main dive suit body (not shown). Glove 10 can be made from a variety of fluid-impermeable wetsuit or drysuit materials without departing from the scope of the present invention. Glove 10 terminates in a wrist seal 10A as is well known in the art.

In general, glove 10 has one or more volumetric regions defined therein with material particles 12 disposed in each of the regions. For example, the illustrated embodiment depicts a contiguous region (defined by dashed lines 11) that includes the palm region and all five fingers. However, it is to be understood that other volumetric regions could be defined in glove 10 without departing from the scope of the present invention. In the present invention, material particles 12 are disposed in region 11 of glove 10 such that material particles 12 are held in position by a material (not shown in FIG. 1) adjacent to corresponding portions of one's hands (not shown) when glove 10 is worn.

Material particles 12 are any of a variety of dry chemical compositions that produce an exothermic reaction in the presence of a gaseous form of oxygen. Typically, material particles 12 will include iron since the iron oxidation process (i.e., iron in the presence of oxygen) is a good exothermic process. As used therein, the term "particles" includes shavings, filings and/or powdered forms of materials. In addition to iron, material particles 12 will typically include one or more other materials such as cellulose, vermiculite, activated carbon, and salt. However, it is to be understood that the particular composition of material particles 12 is not a limitation of the present invention.

Since glove 10 will be used in an underwater environment, there will not be an ambient supply of oxygen to support an exothermic iron oxidation process. In accordance with the present invention, oxygen is supplied to material particles 12 in a controlled fashion to initiate and/or support/sustain an exothermic oxidation process. The controlled supply of oxygen originates from a source 20 of oxygen gas. Typically source 20 is any vessel that stores a gas that includes oxygen as a component portion thereof. Thus, source 20 can contain pure oxygen, air, etc., without departing from the scope of the present invention. One vessel that can be used for source 20 is a pony bottle worn by the diver. However, the present invention is not limited to the use of stored oxygen as source 20 could also be an apparatus that produces oxygen at a sufficient level to support the desired exothermic reaction with material particles 12.

The gas stored/produced by source 20 is dispensed through a valve 22. Control of valve 22 is provided by a valve controller 24 that allows for manual control of valve 22 or provides for automatic control of valve 22 (e.g., a sonic orifice). Manual control of valve 22 will allow a diver to turn the active heating system on or off since the exothermic reaction can be halted/resumed. A flexible line 26 delivers the gas from source 20 to region 11 of glove 10 containing material particles 12. Typically, line 26 leads and is coupled to a port 28 provided in glove 10.

Figure 2:
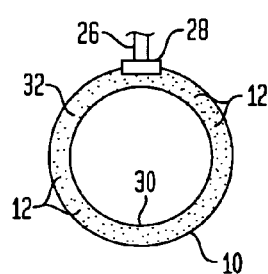
FIG. 2 is a cross-sectional view of the thumb entry region of the diver's glove taken across line 2-2 in FIG. 1.

Material particles 12 can be disposed in region 11 of glove 10 in a variety of ways without departing from the scope of the present invention. Two examples will be explained with additional reference to FIGS. 2 and 3. In FIG. 2, a flexible material 30 is fitted in glove 10 such that a volumetric region 32 is defined between the inner surface of glove 10 and flexible material 30. In this way, glove 10 and flexible material 30 cooperate to define a container for material particles 12 while flexible material defines a thumb sleeve. Flexible material 30 can be fluid-impermeable, gas permeable, or a combination thereof without departing from the scope of the present invention.

Port 28 communicates with region 32 so that the oxygen-containing gas from source 20 can be introduced into region 32 when a diver is underwater. Note that when the supplied oxygen is a component of air, nitrogen gas can build up within region 32. Accordingly, in this type of arrangement, it may be necessary to provide a vent 34 (e.g., a pressure relief valve) in glove 10 that communicates between region 32 and the ambient environment to release the excess gas from region 32. Vent 34 would not be required if pure oxygen was supplied to region 32.

Figure 3:
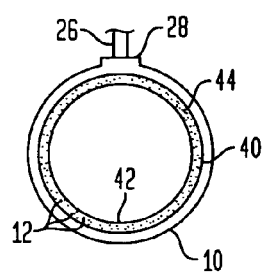
FIG. 3 is a cross-sectional view of the thumb entry region of the diver's glove illustrating another embodiment of the present invention.

FIG. 3 illustrates another way to provide material particles 12 in glove 10. Specifically, a two-layer glove liner has an outer flexible layer 40 and an inner flexible layer 42 spaced apart therefrom to define a region 44 therebetween in which material particles 12 are disposed. The glove liner could be donned by the diver prior to putting on glove 10 so that layer 40 is adjacent to the inside surface of glove 10 and layer 42 defines an open volume that will receive the diver's hand/fingers. Some or all of layer can be made from a gas permeable material so that the oxygen-containing gas passing through port 28 is admitted into region 44. Layer 42 can be gas permeable, gas impermeable, or combination of the two without departing from the scope of the present invention. Note that any gas permeable portions of layer 40 and 42 would be sealed prior to use of the present invention in order to prevent premature initiation of the exothermic reaction.

Figure 4:
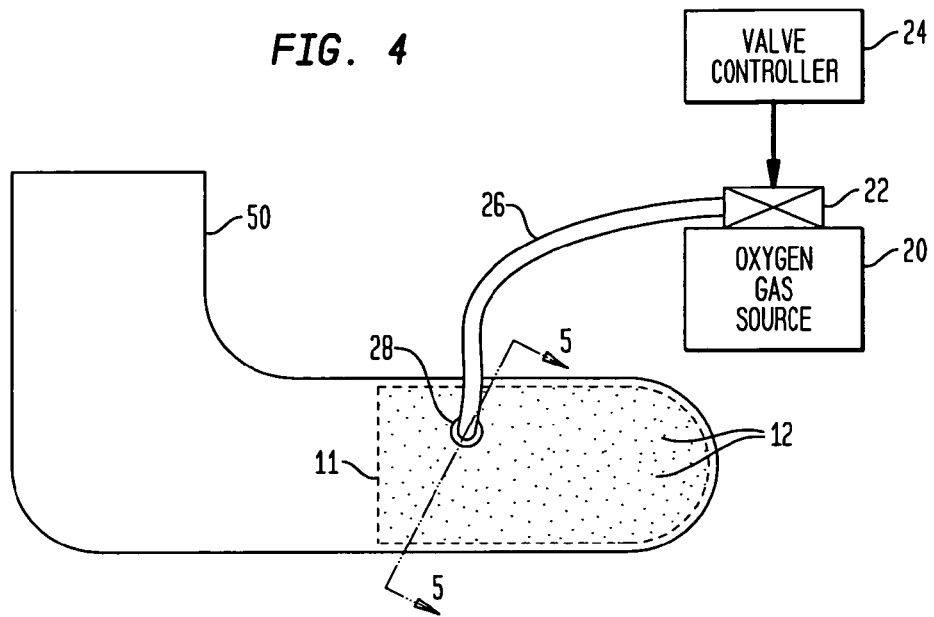
FIG. 4 is a schematic view of an active heating system for an underwater diver's boot in accordance with another embodiment of the present invention.
Figure 5:
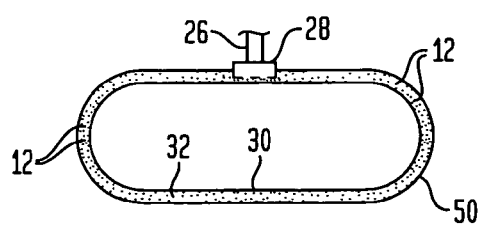
FIG. 5 is a cross-sectional view of the diver's boot taken along line 5-5 in FIG. 4.
Figure 6:
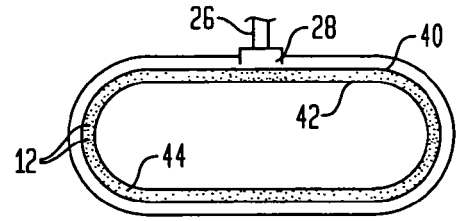
FIG. 6 is a cross-sectional view of the diver's boot illustrating another embodiment of the present invention.

The present invention is not limited to use with a diver's glove as the principles of the present invention can be applied to any portion of a diver's attire (e.g., arms, legs, feet, torso, etc.). For example, FIGS. 4-6 illustrate the principle of the present invention applied to a diver's boot 50. Similar to the glove embodiment described above, the present invention can be used to actively heat one or more regions of the boot 50 (e.g., region 11 that is adjacent to a portion of one's foot or encases a portion of one's foot). Since identical approaches can be used to heat boot 50, identical reference numerals are used in FIGS. 4-6 to indicate the various features of the present invention applied to boot 50. Accordingly, additional description of the embodiments shown in FIGS. 4-6 is not provided herein.

The advantages of the present invention are numerous. The active heating system can be used to provide heat to a variety of an underwater diver's body parts. The system is simple and can be used to heat a diver's extremities for several hours. The system can be fabricated from readily-available and inexpensive components.

Figure 7:
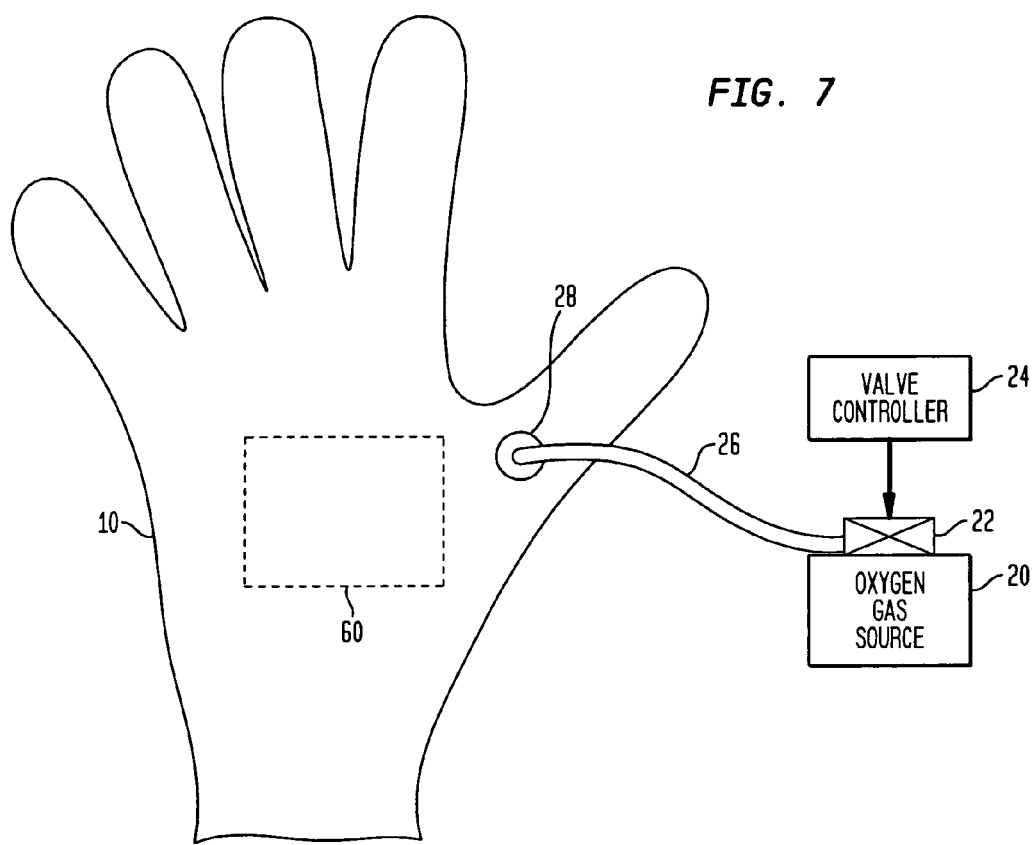
FIG. 7 is a schematic view of an active heating system for a diver's glove utilizing a commercially-available chemical heat pouch in accordance with another embodiment of the present invention.

Although the invention has been described relative to a specific embodiment thereof, there are numerous variations and modifications that will be readily apparent to those skilled in the art in light of the above teachings. For example, FIG. 7 illustrates another embodiment of the present invention where a conventional diver's glove 10 has port 28 formed therein and coupled to source 20 via supply line 26 as described above. However, active heating in glove 10 is provided by the simple inclusion of a commercially-available chemical heat pad/pouch in the palm region of glove 10. That is, pouch 60 is simply placed in the palm region of glove 10.

The exothermic reaction of the material particles (not shown) in pouch 60 is initiated and sustained as the oxygen gas from source 20 is admitted into glove 10. Note that the provision of pouch 60 could also be used in the previously-described embodiments to provide supplemental heat. It is therefore to be understood that, within the scope of the appended claims, the invention may be practiced other than as specifically described.

What is claimed as new and desired to be secured by Letters Patent of the United States is:

1. An active heating system for an underwater diver, comprising:
    an article of clothing adapted to be worn by an underwater diver, said article of clothing having at least one internal region therein;
    material particles disposed within said at least one internal region, said material particles generating heat in an exothermic reaction in the presence of oxygen;
    a source of oxygen gas; and
    means for coupling said source to said at least one internal region wherein said oxygen gas is introduced to said at least one internal region.

2. An active heating system as in claim 1 wherein at least a portion of said material particles comprise iron particles.

3. An active heating system as in claim 1 wherein said means for coupling includes control means for controlling a rate at which said oxygen gas is introduced into said at least one internal region.

4. An active heating system as in claim 3 wherein said control means is manually operated to control said rate.

5. An active heating system as in claim 3 wherein said control means automatically controls said rate.

6. An active heating system as in claim 1
    wherein said source of oxygen gas comprises a vessel containing a supply of air that includes said oxygen gas as a component thereof, and wherein said active heating system further comprises a gas vent for providing gas communication between said at least one internal region and an ambient environment at a specified gas pressure in said selected at least one internal region.

7. An active heating system as in claim 1 wherein said source of oxygen gas consists of oxygen gas in a pure form thereof.

8. An active heating system for an underwater diver, comprising:

an article of clothing adapted to be worn by an underwater diver wherein said article of clothing has an inside surface that faces the body of said underwater diver;

flexible material fitted in at least a portion of said ti inside surface wherein at least one region is defined between one of (i) said inside surface and said flexible material, and (ii) layers of said flexible material;

material particles disposed in each of said at least one region, said material particles generating heat in an exothermic reaction in the presence of oxygen;

a source of oxygen gas; and means for coupling said source to each of said at least one region wherein said oxygen gas is introduced to each said region.

9. An active heating system as in claim 8 wherein at least a portion of said material particles comprise iron particles.

10. An active heating system as in claim 8 wherein said article of clothing is selected from the group consisting of: a wetsuit glove, a wetsuit boot, a drysuit glove, and a drysuit boot.

11. An active heating system as in claim 8 wherein said means for coupling includes control means for controlling a rate at which said oxygen gas is introduced into each of said at least one region.

12. An active heating system as in claim 11 wherein said control means is manually operated to control said rate.

13. An active heating system as in claim 11 wherein said control means automatically controls said rate.

14. An active heating system as in claim 8 wherein said source of oxygen gas comprises a vessel containing a supply of air that includes said oxygen gas as a component thereof, and wherein said active heating system further comprises a gas vent for providing gas communication between each of said at least one region and an ambient environment at a specified gas pressure in each of said at least one region.

15. An active heating system as in claim 8 wherein said source of oxygen gas consists of oxygen gas in a pure form thereof.

16. An active heating system as in claim 8 wherein said flexible material is adapted to conform to the shape of an extremity of the body of the underwater diver.

17. An active heating system as in claim 8 wherein at least a portion of said flexible material comprises a gas permeable material.

* * * * *